(12) United States Patent
Quast et al.

(10) Patent No.: US 6,481,899 B1
(45) Date of Patent: Nov. 19, 2002

(54) OPTICAL CONNECTOR LATCHING MECHANISM FOR A SPECTROPHOTOMETRIC INSTRUMENT

(75) Inventors: Kenneth R. Quast, Hutchinson, MN (US); Mark A. Schmidt, Darwin, MN (US); Sergey I. Gritsenko, Hutchinson, MN (US); Mark S. Lewandowski, Hutchinson, MN (US); Dean E. Myers, Stewart, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 85 days.

(21) Appl. No.: 09/585,487

(22) Filed: Jun. 1, 2000

Related U.S. Application Data
(60) Provisional application No. 60/137,305, filed on Jun. 3, 1999, provisional application No. 60/137,383, filed on Jun. 3, 1999, and provisional application No. 60/137,390, filed on Jun. 3, 1999.

(51) Int. Cl.[7] ................................................. G02B 6/36
(52) U.S. Cl. ........................................................ 385/78
(58) Field of Search ............................. 385/15, 16, 25, 385/56, 58, 60, 70, 72, 78

(56) References Cited

U.S. PATENT DOCUMENTS

| | | | |
|---|---|---|---|
| 3,874,781 A | 4/1975 | Thiel | |
| 4,327,964 A | 5/1982 | Haesly et al. | |
| 4,427,879 A | 1/1984 | Becher et al. | |
| 4,798,440 A | 1/1989 | Hoffer et al. | |
| 4,910,539 A | 3/1990 | Mathis et al. | |
| 4,998,973 A | 3/1991 | Kikuchi | |
| 5,028,113 A | * 7/1991 | Benkan et al. ................. | 385/16 |
| 5,140,663 A | 8/1992 | Edwards et al. | |
| 5,212,748 A | 5/1993 | Curtiss et al. | |
| 5,224,186 A | 6/1993 | Kishimoto et al. | |
| 5,297,227 A | 3/1994 | Brown et al. | |
| 5,456,251 A | 10/1995 | Fiddian-Green | |
| 5,477,853 A | 12/1995 | Farkas et al. | |
| 5,481,634 A | 1/1996 | Anderson et al. | |
| 5,584,296 A | 12/1996 | Cui et al. | |
| 5,719,977 A | 2/1998 | Lampert et al. | |
| 5,879,294 A | 3/1999 | Anderson et al. | |
| 5,896,485 A | 4/1999 | Kirby | |
| 5,902,246 A | 5/1999 | McHenry et al. | |
| 5,923,805 A | 7/1999 | Anderson et al. | |
| 6,062,739 A | * 5/2000 | Blake et al. ................... | 385/76 |
| 6,102,581 A | * 8/2000 | Deveau et al. ................ | 385/56 |
| 6,179,482 B1 | * 1/2001 | Takizawa et al. ............. | 385/81 |
| 6,206,581 B1 | * 3/2001 | Driscoll et al. ............... | 385/78 |
| 6,220,763 B1 | * 4/2001 | Stephenson ................... | 385/73 |
| 6,234,682 B1 | * 5/2001 | Nagaoka et al. .............. | 385/78 |
| 6,238,101 B1 | * 5/2001 | Chen et al. .................... | 385/60 |
| 6,302,591 B1 | * 10/2001 | Nagaoka et al. .............. | 385/59 |

FOREIGN PATENT DOCUMENTS

| | | |
|---|---|---|
| EP | 0 367 737 A2 | 10/1989 |
| EP | 0 476 596 | 3/1992 |
| GB | 1386734 | 3/1975 |
| GB | 1558643 | 1/1980 |

* cited by examiner

*Primary Examiner*—Brian Sircus
*Assistant Examiner*—Thanh-Tam Le
(74) *Attorney, Agent, or Firm*—Faegre & Benson LLP (57) ABSTRACT

An optical connector latch to optically couple at least one optical fiber ferrule on an interface housing with an optics receptacle mount on an instrument and a method of using the same. The optical connector latch comprises one or more shell pegs adapted to advance the interface housing into engagement with the optics receptacle mount. One or more ferrule pins are adapted to extend through latch holes in the interface housing and latch holes in the optics receptacle mount to engage with the optical fiber ferrule. A drive mechanism is provided to drive the shell pegs and the ferrule pins toward the optics receptacle mount.

18 Claims, 13 Drawing Sheets

OPTICAL CONNECTOR LATCHING MECHANISM FOR A SPECTROPHOTOMETRIC INSTRUMENT

The present application claims the benefit of U.S. Provisional Application Ser. No. 60/137,305 entitled "Optical Connector Latching Mechanism for a Spectrophotometric Instrument"; U.S. Provisional Application Ser. No. 60/137,383 entitled "Disposable Tissue Probe Tip"; and U.S. Provisional Application Ser. No. 60/137,390 entitled "Fiber Optic Light Mixer", all filed on Jun. 3, 1999.

FIELD OF THE INVENTION

The present invention relates generally to mechanisms for optically coupling optical connectors to one another, and in particular, to an optical connector latching mechanism that is substantially insensitive to external forces.

BACKGROUND OF THE INVENTION

Optical fibers are used in a variety of applications ranging from simple light displays to medical instruments and high-speed data transmission. Frequently, it is necessary to interconnect one section of optical fiber to another section in a manner that might be likened to the interconnection or splicing of one electrical wire to another. The interconnections of one optical fiber to another are more complex since precise alignment of the ends of one optical fiber with the end of another optical fiber in the connector must be made in order to retain a high efficiency of light transmission through the connection.

When releasable connection of one end or the terminal end of an optical fiber to an optical fiber tool, which may be in the form of a releasable connector or the like, is required, the alignment problem is compounded by the requirement for continued precision connections being maintained, even after many connections and disconnections have been made.

A greater degree of complexity exists when two or more fiber optic cables, such as in a duplexed fiber optic cable, must be interconnected to align the optical fibers in each of the cable terminators or in a cable terminator and a releasable working head of some type, since any misalignment of the optical fibers in the two portions being interconnected causes a significant reduction in the efficiency of light transmission through the connector. Essentially, such connections need to be made with nearly zero tolerance so that misalignment does not take place. Additionally, the quality of the optical signal received by the monitor can change due to vibration or other external forces applied to the optical interface connection. Although a number of optical connector and latching mechanisms are commercially available or otherwise known, there is a continuing need for improved optical connector latching mechanisms.

BRIEF SUMMARY OF THE INVENTION

The present invention relates to an optical connector latch to optically couple at least one optical fiber ferrule on an interface housing with an optics receptacle mount on an instrument. In one embodiment, the optical connector latch comprises one or more shell pegs adapted to advance the interface housing into engagement with the optics receptacle mount. One or more ferrule pins are adapted to extend through latch holes in the interface housing and latch holes in the optics receptacle mount to engage with the optical fiber ferrule. A drive mechanism is provided to drive the shell pegs and the ferrule pins toward the optics receptacle mount.

The drive mechanism may include an operator-actuated handle. The drive mechanism may also include one or more cams mechanically coupled to the shell pegs and ferrule pins. In one embodiment, the drive mechanism causes the shell pegs to advance the interface housing into engagement with the optics receptacle mount before the ferrule pins are engaged with the optical fiber ferrules. The ferrule pins may extend through the shell pegs. In one embodiment, the shell pegs have tapered heads. The ends of the ferrule pins typically include a shape corresponding to a shape of the optical fiber ferrules.

The drive mechanism may include an over-center latch. The shell peg and/or ferrule pins may include springs adapted to bias them toward the interface housing. The interface housing and optics receptacle mount typically comprise a nested configuration when optically coupled. An electrical connector may also be electrically coupled when the interface housing is advanced into engagement with the optics receptacle mount. The present optical connector latch mechanism can optically couple a plurality of optical fiber ferrules simultaneously.

The present invention is also directed to a method of optically coupling at least one optical fiber ferrule on an interface housing with an optics receptacle mount on an instrument. The method includes the steps of inserting one or more shell pegs into the interface housing and advancing the interface housing into engagement with the optics receptacle mount; and extending one or more ferrule pins through latch holes in the interface housing and latch holes in the optics receptacle mount into engagement with the optical fiber ferrule. In one embodiment, the shell pegs are advanced into engagement with the optics receptacle mount before advancing the ferrule pins into engagement with the optical fiber ferrules.

DETAILED DESCRIPTION OF THE INVENTION

The present invention relates to an optical connector latch mechanism that securely and accurately, yet releasably, couples optical components in a manner that is substantially insensitive to external forces. While the present optical connector latch mechanism can be used for a variety of applications, the releasable optical connection between a probe connector and a monitor in a spectrophotometric instrument, such as the instrument disclosed in U.S. Pat. No. 5,879,294 (Anderson et al.), is used to illustrate the present invention.

Figure 1:
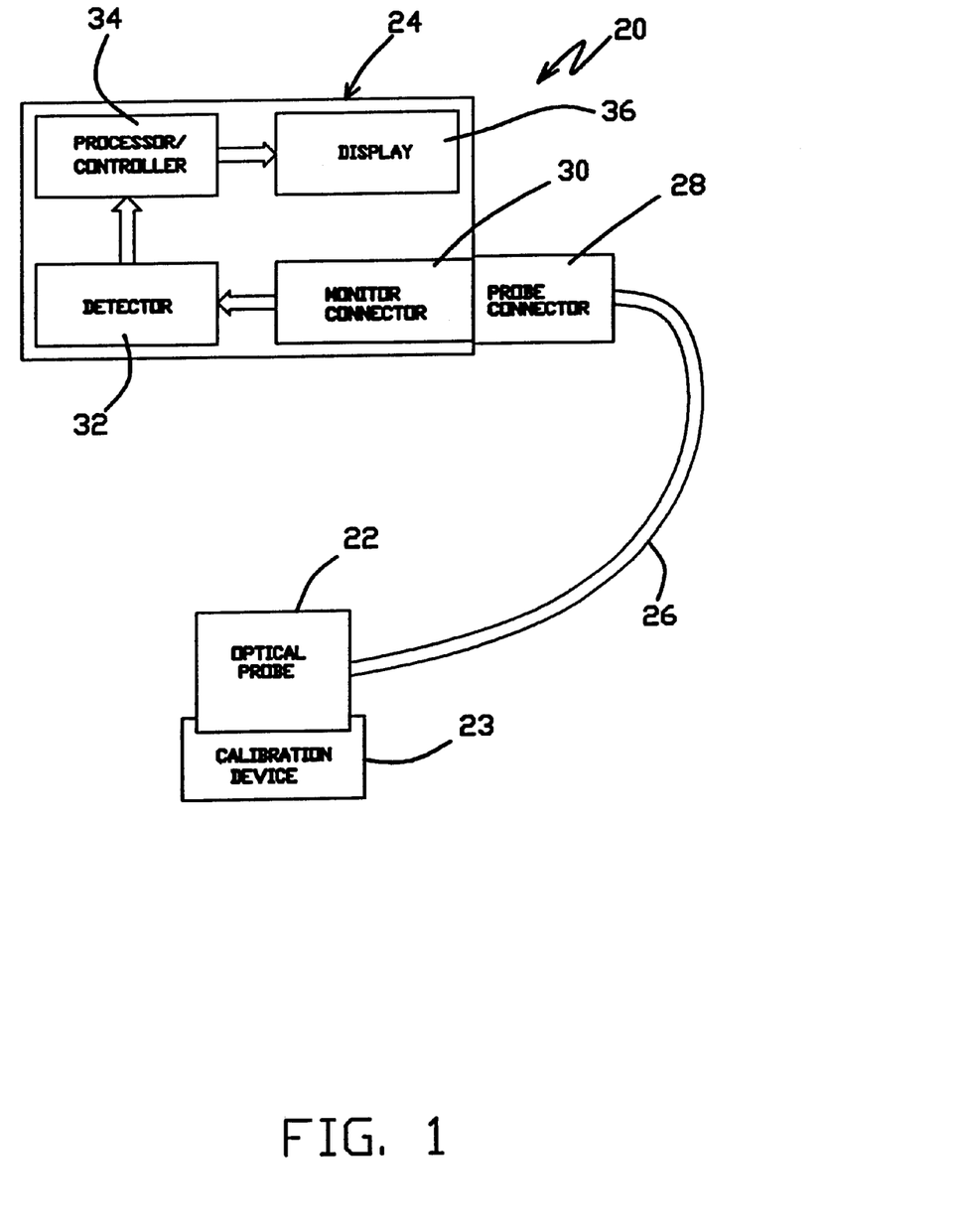
FIG. 1 is a schematic illustration of an exemplary instrument that can use the optical connector latch mechanism of the present invention.

By way of illustration only, the operation of an instrument of this type is described briefly with reference to FIG. 1. The instrument 20 includes an optical probe 22 that is releasably connected to an electronics package or monitor 24. In operation, the optical probe 22 is positioned on the tissue to be measured or on a calibration device 23. The optical probe 22 is interfaced to the monitor 24 through optical fibers 26 and a probe connector 28. The probe connector 28 includes light emitting diodes (LED's) or other light sources for generating light at a number of different wavelengths (see FIG. 2). The light used to measure characteristics of the tissue is coupled to the optical probe 22 by send-optical fibers 26. After being transmitted from the tissue-engaging surface of the optical probe 22 into the tissue being measured, the light travels through the tissue before being collected at the end of the receive optical fiber 26. The collected light (measurement or sample light signal) is then transmitted to the monitor 24 through the probe connector 28 and monitor connector 30. A reference light signal corresponding to each of the measurement light signals (i.e., the reference light signals are not transmitted through the tissue) is also transmitted to the monitor connector 30.

The ends of the optical fibers 26 from the optical probe 22 are typically terminated at ferrules in the probe connector 28. The ferrules are adapted to plug into or otherwise mate with associated connectors (i.e., an optics receptacle mount) in the monitor connector 30. The optical probe 22 is described in greater detail in the co-pending and commonly assigned U.S. Provisional Application Ser. No. 60/137,383 entitled "Disposable Tissue Probe Tip" and U.S. Provisional Application Ser. No. 60/137,390 entitled "Fiber Optic Light Mixer", both filed on Jun. 3, 1999. In one embodiment, the probe connector 28 generates a calibration recognition signal at 530 nanometers and measurement light signals at 680, 720, 760 and 800 nanometers.

The collected measurement light signals and reference light signals received by the monitor 24 are transmitted to a detector 32 which produces electrical signals representative of these light signals at each wavelength of interest. A processor/controller 34 then processes these signals to generate data representative of the measured tissue parameter (e.g., saturated oxygen level ($StO_2$)). The measurement reading can be visually displayed on a display 36. Algorithms used to compute the tissue parameter data are generally known and described in U.S. Pat. No. 5,879,294 (Anderson et al.).

Figure 2:
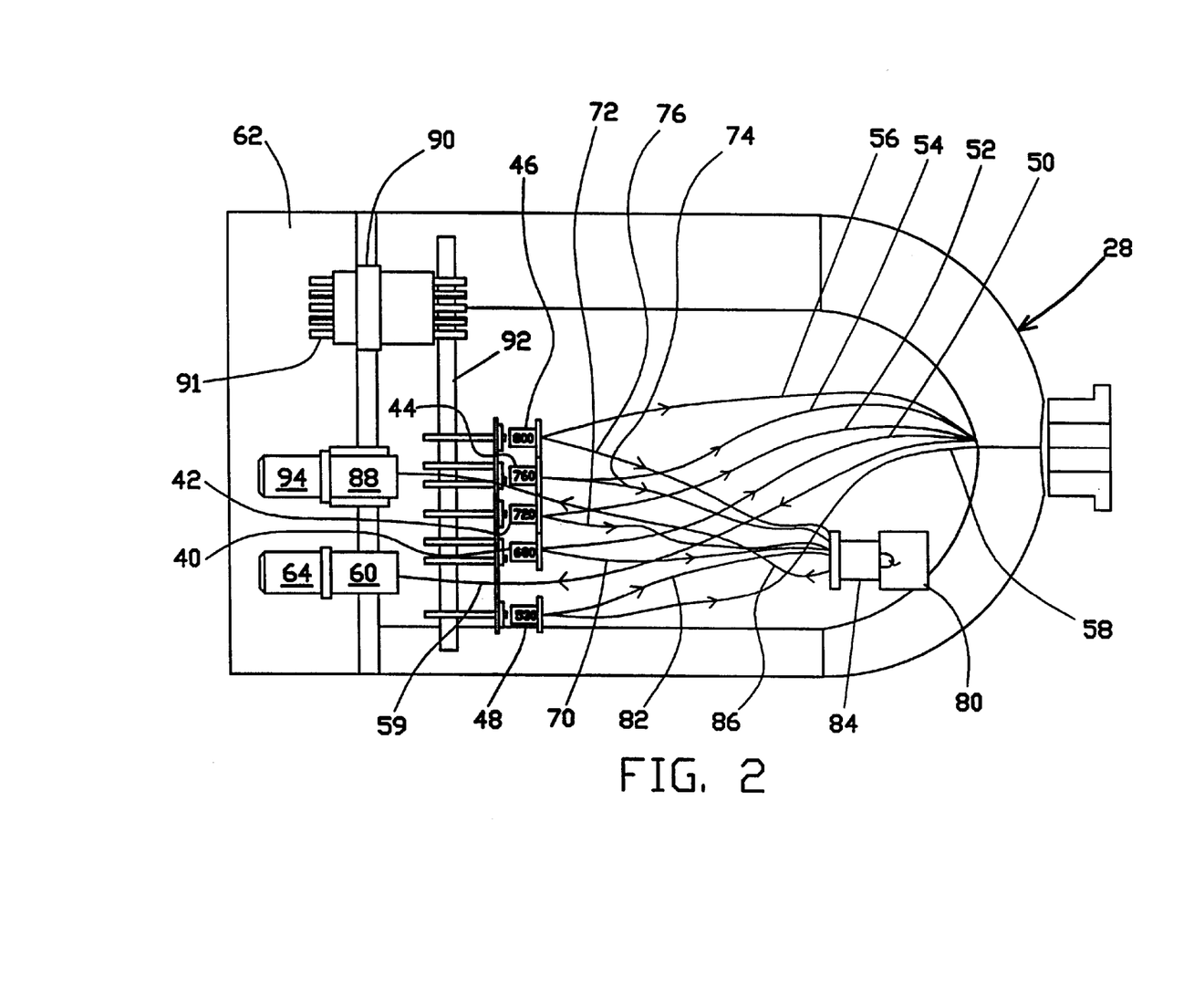
FIG. 2 is a side sectional view of a probe connector in accordance with the present invention.

FIG. 2 is a sectional view of an exemplary probe connector 28 suitable for use in the present invention. As shown, the probe connector 28 includes 4 LED's 40, 42, 44, 46 for generating the measurement light signals at 680, 720, 760, and 800 nanometers, respectively. Light signals from each of these LED's 40, 42, 44,46 are couples to the optical probe 22 by separate measurement signal send fibers 50, 52, 54, 56. Light from a calibration recognition LED 48 is couples to the optical probe 22 by a separate calibration recognition send fiber 58. After being transmitted through the tissue being analyzed and collected at the optical probe 22, the measurement light signal is coupled back to the probe connector 28 by a measurement or sample signal receive fiber 59. The end of the measurement signal receive fiber 59 terminates at a sample ferrule fiber terminal 60 located in an interface housing 62. The sample ferrule fiber terminal 60 includes a sample ferrule 64 adapted to mate with a socket in the monitor connector 30, as will be discussed below.

A reference light signal is also provided by the probe connector 28. The reference light signal includes a portion of the light from each of the LED's 40, 42, 44, 46. In the embodiment shown in FIG. 2, the reference light signal is collected by a reference light signal send optical fibers 70, 72, 74, 76 that extend from each measurement light signal source LED's 40, 42, 44, 46 to a light mixer 80 formed from a scattering material. Light from the calibration recognition LED 48 is coupled to the light mixer 80 by calibration reference light signal send optical fiber 82. A ferrule 84 is typically used to optically couple the optical fibers 70, 72, 74, 76, 78 to the light mixer 80. The reference light received from each LED 40, 42, 44, 46, 48 is mixed and attenuated at the light mixer 80 and transmitted through the reference signal receive fiber 86 to a reference ferrule fiber terminal 88 located in the interface housing 62. Since light from measurement signal send fibers 40, 42, 44, 46 is transmitted through the tissue, the intensity of the measurement light signal at the sample ferrule 64 is much less than the intensity of the non-attenuated reference light signal at the reference ferrule 88 (e.g., about 1 million times less). This mismatch in signal magnitude requires the reference signal to be attenuated in order to measure the light signals with a common detector gain control setting. The reference ferrule fiber terminal 88 includes a reference ferrule 94 adapted to mate with a socket in the monitor connector 30, as will be discussed below.

The interface housing 62 also includes a conventional electrical connector 90 that is electrically coupled to the LED's 40, 42, 44, 46, 48, typically through the use of a printed circuit board 92. The electrical connector 90 includes a plurality of contacts or pins 91. The electrical connector 90 couples with the monitor connector 30 and provides electric power and control signals to the LED's 40, 42, 44, 46, 48. Although the probe connector 28 is illustrated with two output fibers (ferrules 64, 94) coupled to the monitor connector, the present optical connector latch mechanism can be used for optical connectors with one or more output fibers.

Figure 3:
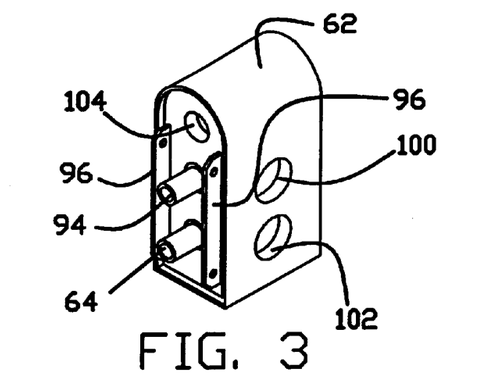
FIG. 3 is a perspective view of an interface housing used in a probe connector in accordance with the present invention.

FIG. 3 is a rear view of the interface housing 62 of the probe connector 28. Reference ferrule fiber terminal 94 and sample ferrule fiber terminal 64 are shown without the reference signal receive fiber 86 and measurement signal receive fiber 59 attached, respectively. Brackets 96 are provided for attaching the interface housing 62 to the body of the probe connector 28. An electrical connector access hole 104 is provided in the interface housing 62 for the electrical connector 90 (see FIG. 2).

Figure 4:
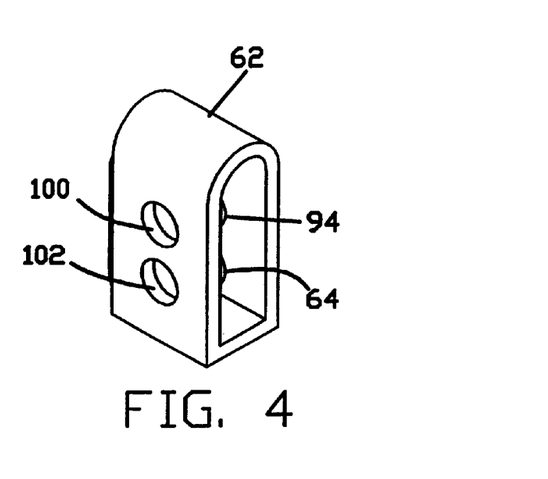
FIG. 4 is a perspective view of the interface housing of FIG. 3 from the opposite direction.

FIG. 4 is a front view of the interface housing 62 of FIG. 3. The interface housing 62 includes two or more latch holes 100, 102 positioned adjacent to the reference ferrule 94 and sample ferrule 64, respectively. In the embodiment illustrated in FIG. 4, the latch holes 100, 102 are oriented perpendicular to the orientation of the reference ferrule 94 and sample ferrule 64. The number of latch holes and the orientation of the latch holes can vary depending upon the application.

Figure 5:
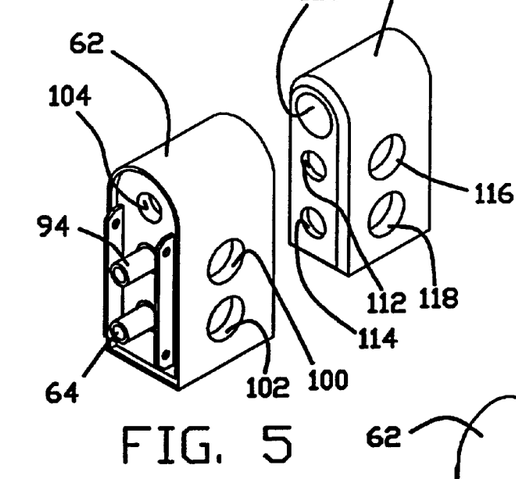
FIG. 5 is a perspective view of the interface housing of FIG. 3 positioned opposite a mating optics receptacle mount in accordance with the present invention.
Figure 6:
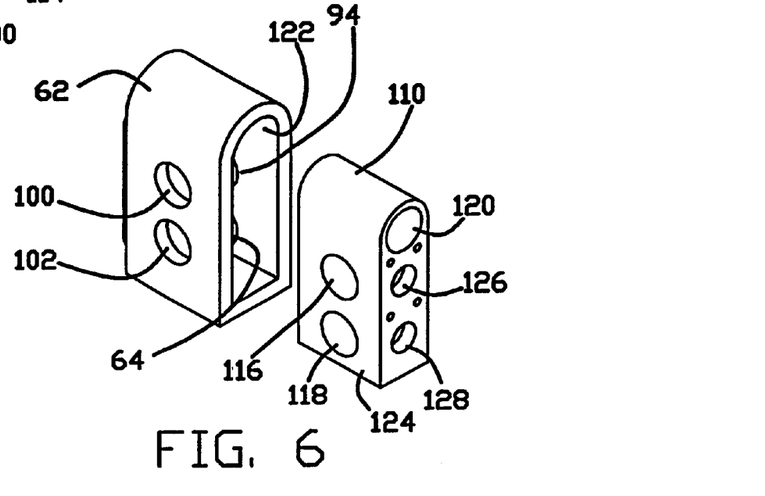
FIG. 6 is a perspective view of the interface housing and mating optics receptacle mount of FIG. 5 viewed from the opposite direction.

FIGS. 5 and 6 are perspective views of the interface housing 62 portion of the probe connector 28 positioned opposite and optics receptacle mount 110 portion of the monitor connector 30. The monitor connector 30 is preferably rigidly mounted in the monitor 24. The optics receptacle mount 110 is typically rigidly mounted in the monitor connector 30 (see FIG. 9A). The optics receptacle mount includes a reference ferrule socket 112 and sample ferrule socket 114 arranged to couple with the reference ferrule 94 and the sample ferrule 64. The optics receptacle mount 110 also includes a pair of latch holes 116, 118 arranged to correspond with the latch holes 100, 102 on the interface housing 62. An electrical connector socket 120 is also provided in the optics receptacle mount 110 that is aligned with the electrical connector access hole 104 and retains the mating portion for the electrical connector 90.

As best illustrated in FIG. 6, the reference ferrule socket 112 extends through the optics receptacle mount 110 and exits at a detector reference receptacle 126. Similarly, the sample ferrule socket 114 extends through the optics receptacle mount 110 and exits at a detector sample socket 128. The detector reference socket 126 and the detector sample socket 128 optically couple the optics receptacle mount 110 to the detector 32.

The optics receptacle mount 110 has an outer shape 124 that permits nesting with an opening 122 in the interface housing 62. Consequently, when the interface housing 62 is inserted onto the optics receptacle mount 110, the reference ferrule 94 extends into the reference ferrule socket 112 to generally optically couple with the detector reference socket 126. The sample ferrule 64 extends into the reference ferrule socket 114 to generally optically couple with the detector sample socket 128. Additionally, the latch holes 100, 102 on the interface housing 62 are generally aligned with the latch holes 116, 118 on the optics receptacle mount 110.

Figure 7:
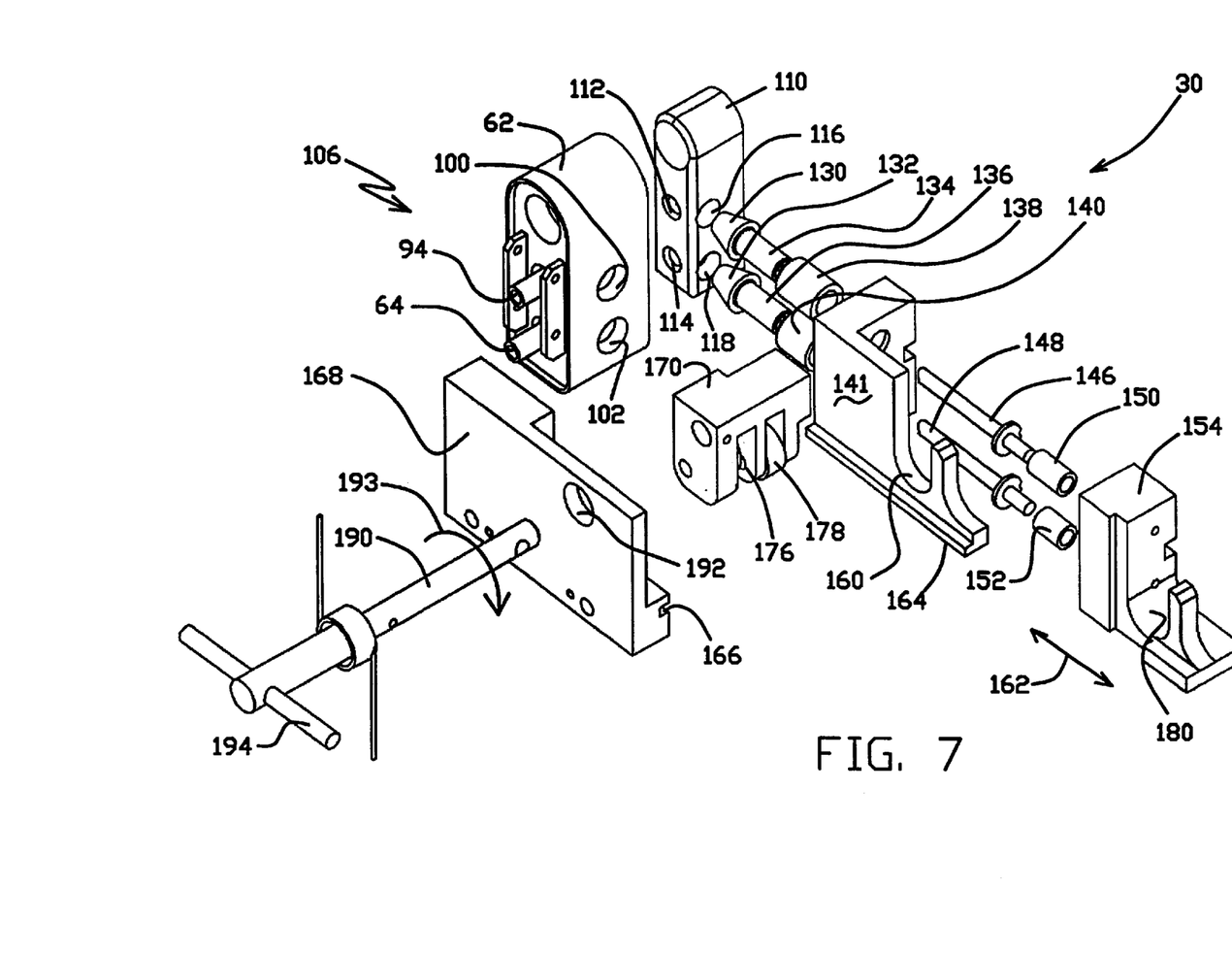
FIG. 7 is an exploded view of an optical connector latch mechanism in accordance with the present invention.
Figure 8:
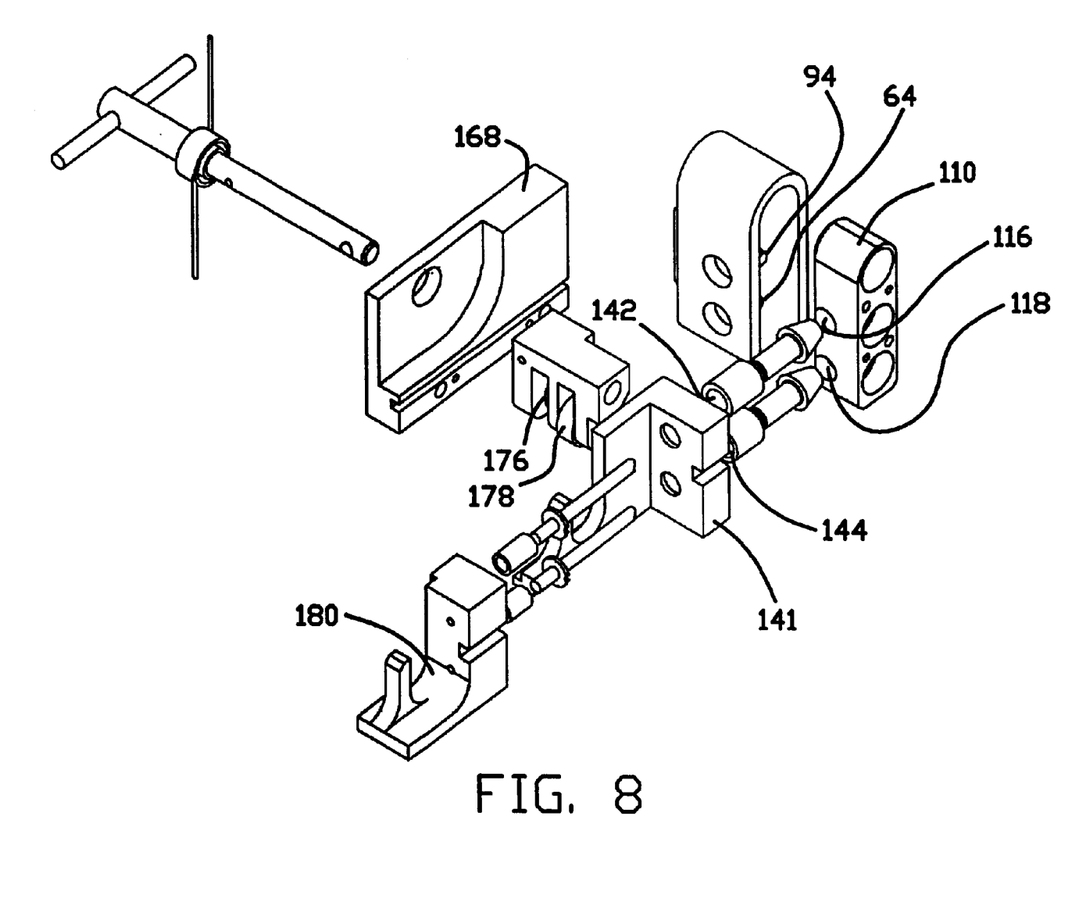
FIG. 8 is a perspective view of FIG. 7 seen from the opposite direction.

FIGS. 7 and 8 are exploded perspective views of an optical connector latch mechanism 106 in accordance with the present invention. The monitor connector 30 is illustrated without the optical interface with the detector 32 and the interface housing 62 is shown without the reference signal received fiber 86 connected to the reference ferrule fiber terminal 94 or the measurement signal receive fiber 59 connected to the sample ferrule fiber terminal 64 (see FIG. 2).

The monitor connector 30 illustrated in FIGS. 7 and 8 includes the optics receptacle mount 110 with the reference ferrule socket 112 and sample ferrule socket 114 oriented opposite the reference ferrule 94 and sample ferrule 64 on the interface housing. Latch holes 116, 118 are positioned opposite shell peg heads 130, 132, respectively. The shell peg heads 130, 132 are mounted on shafts 134, 136 that are biased towards the optics receptacle mount 110 by springs 138, 140, respectively. The shell peg heads 130, 132, the shafts 134, 136 and the springs 138, 140 are mounted to shell peg block 141. The shell peg heads, 130, 132, shafts 134, 136 and springs 138, 140 each have a center opening 142, 144 for receiving ferrule pins 146, 148. The ferrule pins 146, 148 are biased towards the optics receptacle mount 110 by ferrule pin springs 150, 152 that abut ferrule block 154. The ferrule pins 146, 148 preferably each have a notch 206, 208 or other shaped feature at the distal ends to optimize engagement with the ferrules 64, 94. The ferrule pins 146, 148 may also have flat ends without the notches 206, 208.

Shell peg block 141 includes a ridge 164 that engages with a slot 166 on support bracket 168. Shell peg block 141 and ferrule block 154 slide along an axis 162 so that the shell peg heads 130, 132 and the ferrule pins 146, 148 can engage and disengage with the latch holes 116, 118, respectively. Although the shell peg heads 130, 132 and latch holes 116, 118 are illustrated as being tapered or conical in shape, any of a variety of other shapes can be used to achieve a positive latch.

Bearing block 170 includes shell peg cam 176 that engages with shell peg cam engaging surface 160. Finally, bearing block 170 includes ferrule cam 178 that engages with ferrule cam engaging surface 180. Handle shaft 190 extends through opening 192 in the support bracket 168 and engages with bearing block 170. The various cam surfaces 176, 178 have a common shaft 190 so that a single actuation by the user (rotation of the shaft 190) can actuate both the tapered shell peg heads 130, 132 and the ferrule pins 146, 148. Handle 194 is optionally provided for applying a torque to the handle shaft 190. As the handle shaft 190 is rotated in the direction 193, the various cam surfaces 176, 178 simultaneously advance the shell peg block 141 and ferrule block 154 towards the optics receptacle mount 110. In an alternate embodiment, the handle 194 and/or the bearing block 170 can be replaced by a variety of actuators to advance the shell peg block 141 and ferrule block 154, such as a rotary or linear motor, solenoid, pneumatic or hydraulic cylinder, and the like. For example, a motor can be used to apply torque to the handle shaft 190 or one or more actuators can be used to advance the shell peg block 141 and ferrule block 154, without the bearing block 170.

FIGS. 9–12 illustrate operation of the present optical connector latch 106 through various stages of engagement. The present optical connector latch mechanism 106 is designed to draw the interface housing 62 into the monitor connector 30 and to fully engage the reference ferrule 94 and sample ferrule 64 with the reference ferrule socket 112 and sample ferrule socket 114. Once the interface housing 62 is firmly engaged with the monitor connector 30, the present optical connector latch mechanism 106 presses against the reference ferrule 94 and sample ferrule 64 to form a stable and secure optical coupling with the detector 32 through the detector reference socket 126 and the detector sample socket 128, respectively.

Figure 9A:
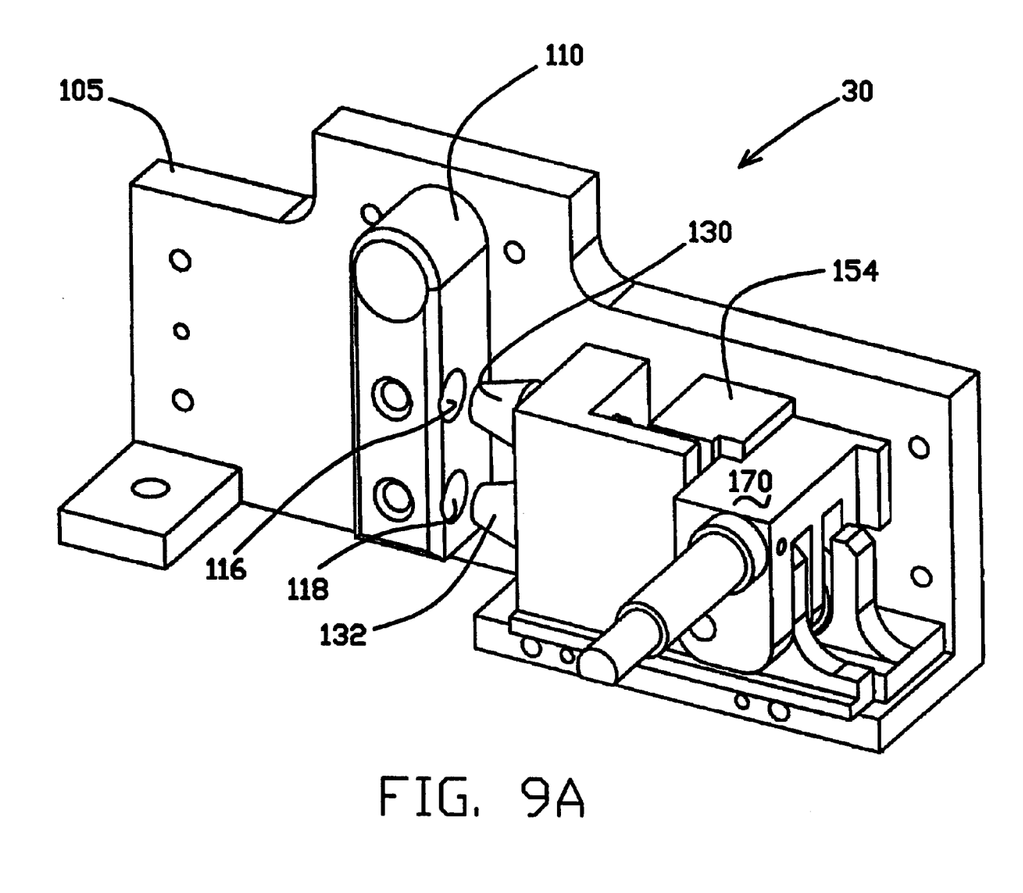
FIG. 9A is a perspective view of an optical connector latch mechanism in the fully disengaged position in accordance with the present invention.

FIG. 9A illustrates the monitor connector 30 in the disengaged position with the support bracket 168 removed. The optics receptacle mount 110 is mounted to bulkhead 105. The bearing block 170 is seated against the ferrule block 154 so that the shell peg heads 130, 132 are aligned with the latch holes 116, 118 but separated from the optics receptacle mount 110.

Figures 9B, 9C:
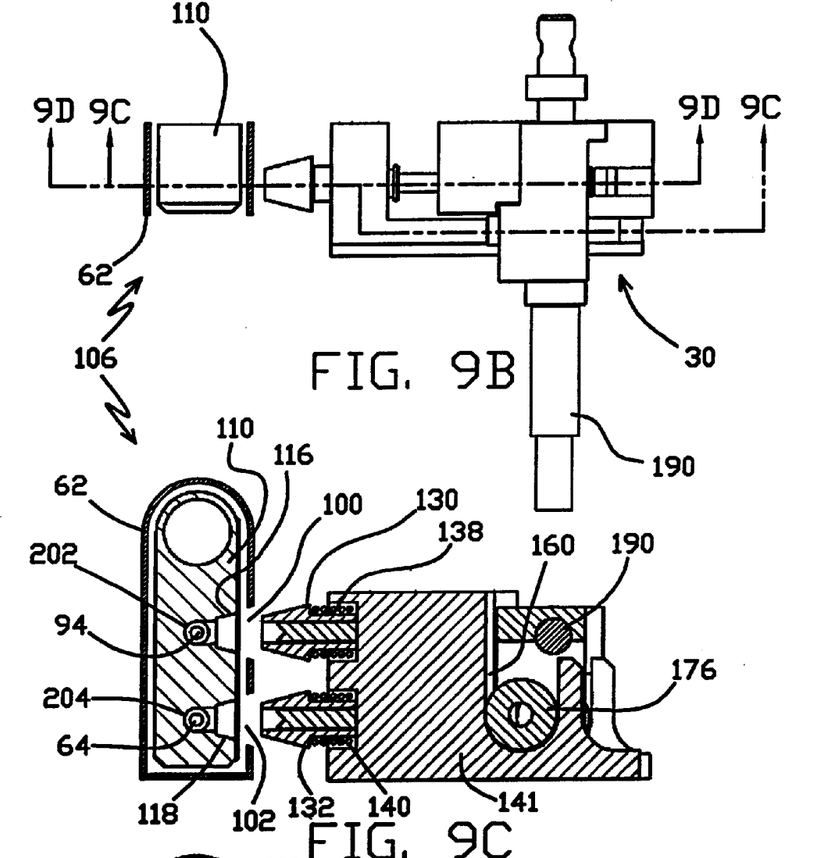
FIG. 9B is a top view of the optical connector latch mechanism of FIG. 9A.
FIG. 9C is a sectional view of FIG. 9B through the bearing block.
Figure 9D:
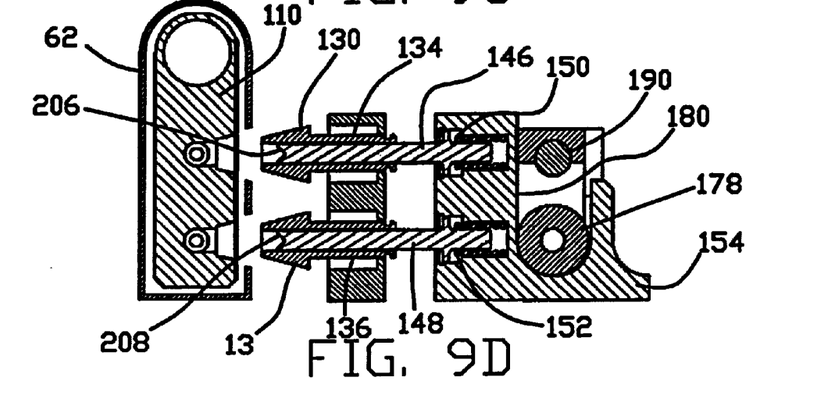
FIG. 9D is a sectional view of FIG. 9B through the ferrule block.

FIGS. 9B–9D illustrate the optical connector latch mechanism 106 with the interface housing 62 engaged with the optics receptacle mount 110 in a nested configuration. The interface housing 62 is pressed against the optics receptacle mount 110 until the ferrules 94, 64 bottom-out in the reference ferrule socket 112 and sample ferrule socket 114, respectively. The latch holes 100,102 are generally in position for the shell peg heads 130, 132 to be inserted.

As best illustrated in FIG. 9C, the shell peg heads 130, 132 are positioned opposite the latch holes 110, 102 in the interface housing 62 and the tapered latch holes 116, 118 in the optics receptacle mount 110. Springs 138, 140 bias the shell peg heads 130, 132, respectively, toward the optics receptacle mount 110. The reference ferrule 94 and sample ferrule 64, that normally extend in the opening 122 of the interface housing 62 in a cantilever fashion, are abutted against surfaces 202, 204, respectively, on the optics receptacle mount 110. The shell peg cam 176 is engaged with the shell peg cam engaging surface 160 of the shell peg block 141.

FIG. 9D is cross-section of FIG. 9B through the ferrule pins 146, 148. As discussed above, the ferrule pins 146, 148 extend through the shell pegs heads 130, 132 and the shafts 134, 136, respectively. The ferrule pins 146, 148 are biased towards the optics receptacle mount 110 by springs 150, 152. Ferrule cam 178 is positioned to engage with ferrule cam engaging surface 180 on the ferrule block 154 when a torque is applied to the shaft handle 190.

The shell peg block 141 and ferrule block 154 preferably travel further than the desired motion of the shell peg heads 130, 132 or the ferrule pins 146, 148. When the shell peg heads 130, 132 or the ferrule pins 146, 148 contact interface housing 62 or the ferrules 64, 94, the springs 138, 140, 150, 152 are preferably compressed while the shell peg block 141 and ferrule block 154 continue to advance toward the optics receptacle mount 110. This arrangement assures that the interface housing 62 and ferrules 64, 94 will be latched. One or both sets of the springs 138,140 or 150, 152 also provide a reaction force for over-center latching function discussed below.

The ferrule pins 146, 148 include notches 206, 208 to optimize engagement with the reference ferrule 94 and sample ferrule 64. The shape of the notches 206, 208 may vary depending upon the shape of the reference ferrule 94 and the sample ferrule 64.

Figure 10A:
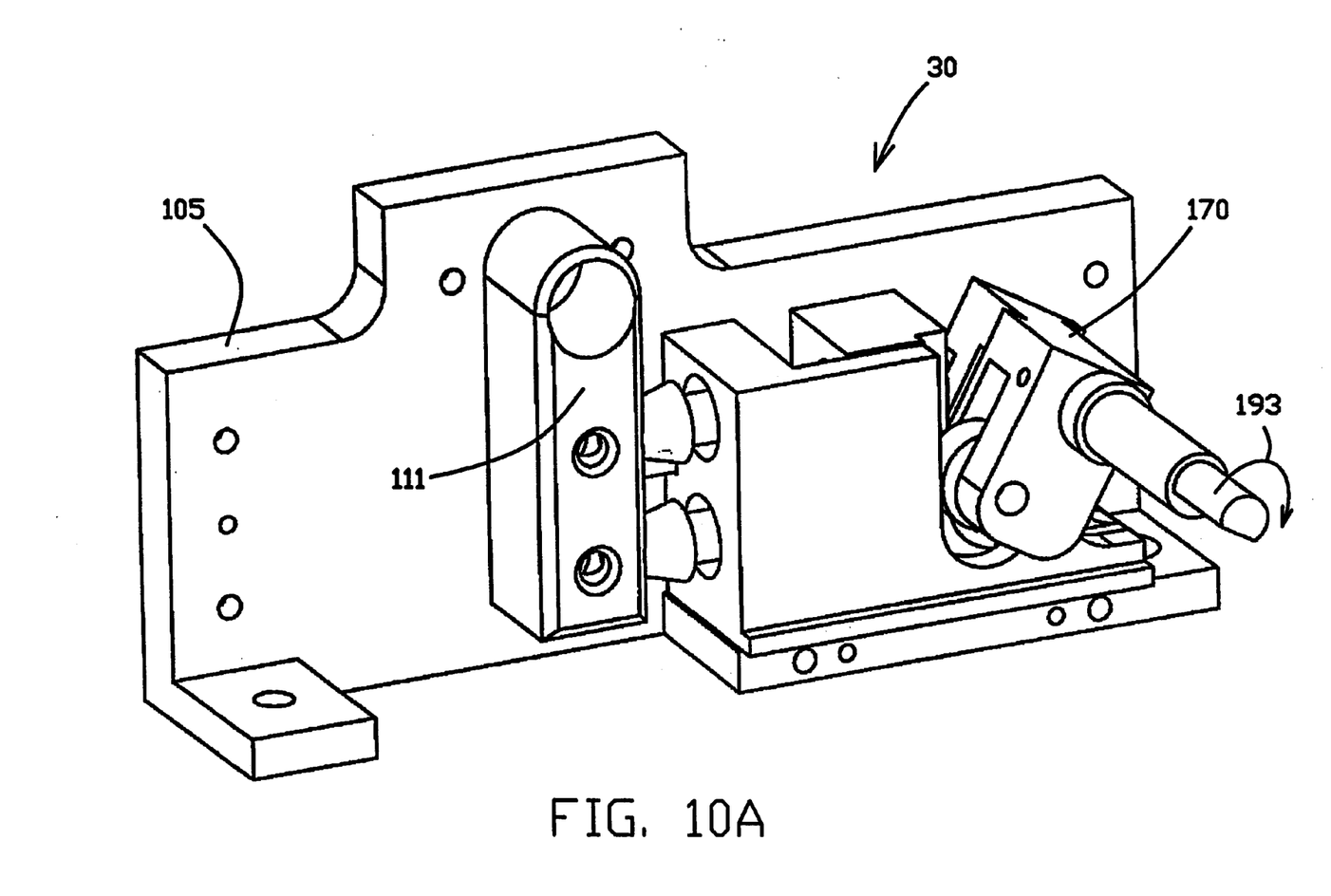
FIG. 10A is a perspective view of the optical connector latch mechanism of FIG. 9A with the bearing block advanced 30 degrees in accordance with the present invention.

FIG. 10A illustrates the monitor connector 30 of the present invention with the bearing block 170 rotated approximately 30 degrees in the direction 193. The support bracket 168 is fixed relative to the bulk head 105 so that rotation of the handle shaft 190 in the hole 192 will cause the bearing block 170 to rotate as shown in FIG. 10A, with the resulting cam forces being applied to the shell peg block 141 and ferrule block 154.

Figures 10B, 10C:
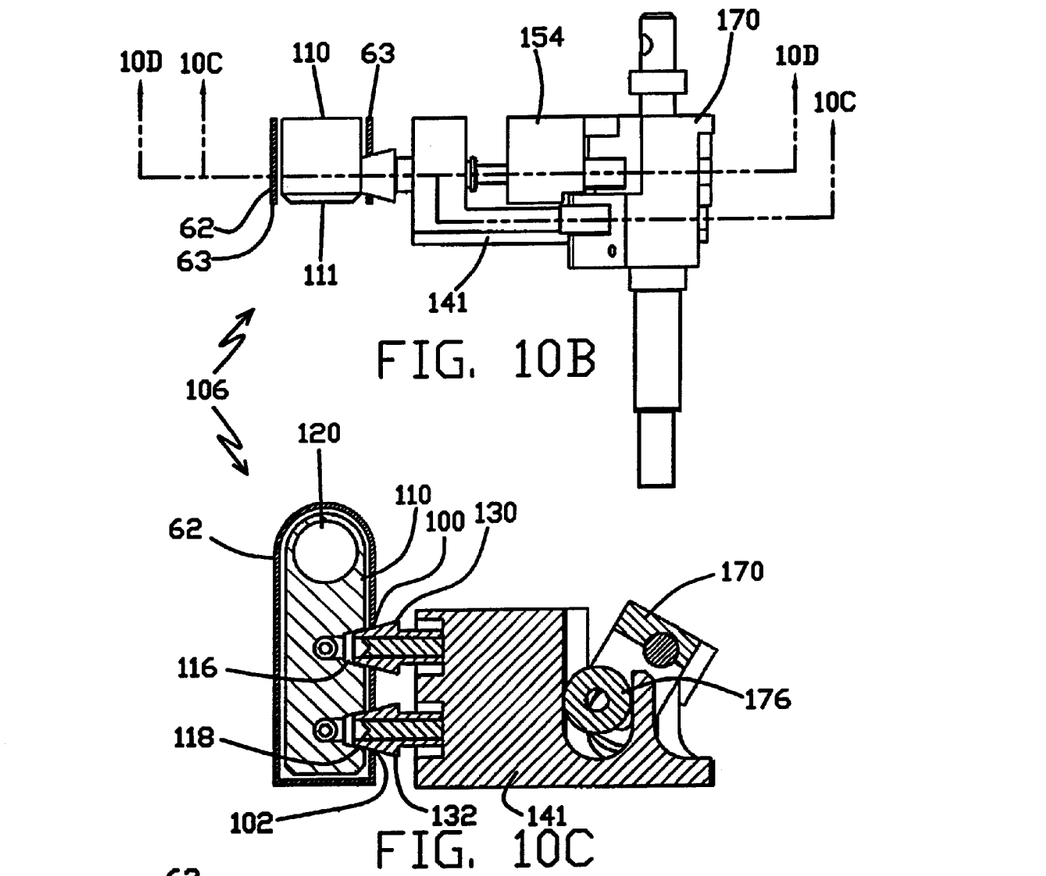
FIG. 10B is a top view of the optical connector latch mechanism of FIG. 10A.
FIG. 10C is a sectional view of FIG. 10B through the bearing block.
Figure 10D:
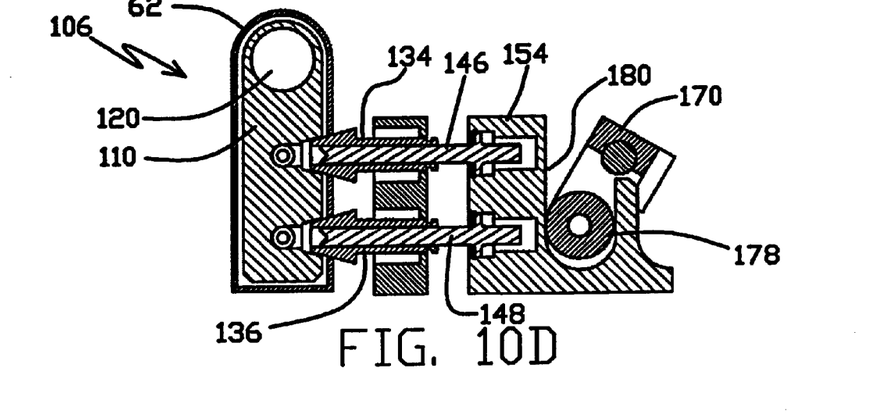
FIG. 10D is a sectional view of FIG. 10B through the ferrule block.

FIGS. 10B–10D illustrate the optical connector latch mechanism 106 with the interface housing 62 engaged with the optics receptacle mount 110 in a nested configuration. The shell peg cam 176 advances the shell peg block 141 towards the optics receptacle mount 110 and interface housing 62. The shell peg heads 130, 132 are advanced through the latch holes 100, 102 in the interface housing 62 and into a mating relationship with tapered latch holes 116, 118 in the optics receptacle mount 110. The leading edges of the shell peg heads 130, 132 forces the interface housing 62 forward to positively engage with the optics receptacle mount 110. In one embodiment, the interface housing 62 is seated against flat surface 111 on the optics receptacle mount 110. Alternatively, the leading edge 63 of the interface housing 62 can be seated against the bulkhead 105. Simultaneously, pins 91 on electrical connector 90 are forced into engagement with a mating structure in the electrical connector socket 120.

Rotation of the bearing block 170 simultaneously causes the ferrule cam 178 to positively engage with the ferrule cam engaging surface 180 to advance the ferrule block 154 towards the optics receptacle mount 110. Movement of the ferrule block 154 advances the notched ferrule pins 146, 148 through the shafts 134, 136 and towards the optic receptacle mount 110. The motion of the ferrule pins 146, 148 is independent of the motion of the shell peg heads 130, 132, but in the same direction. In the preferred embodiment, the ferrule pins 146, 148 do not firmly engage the ferrules 64, 94 until after the shell peg heads 130, 132. are fully advanced.

Figure 11A:
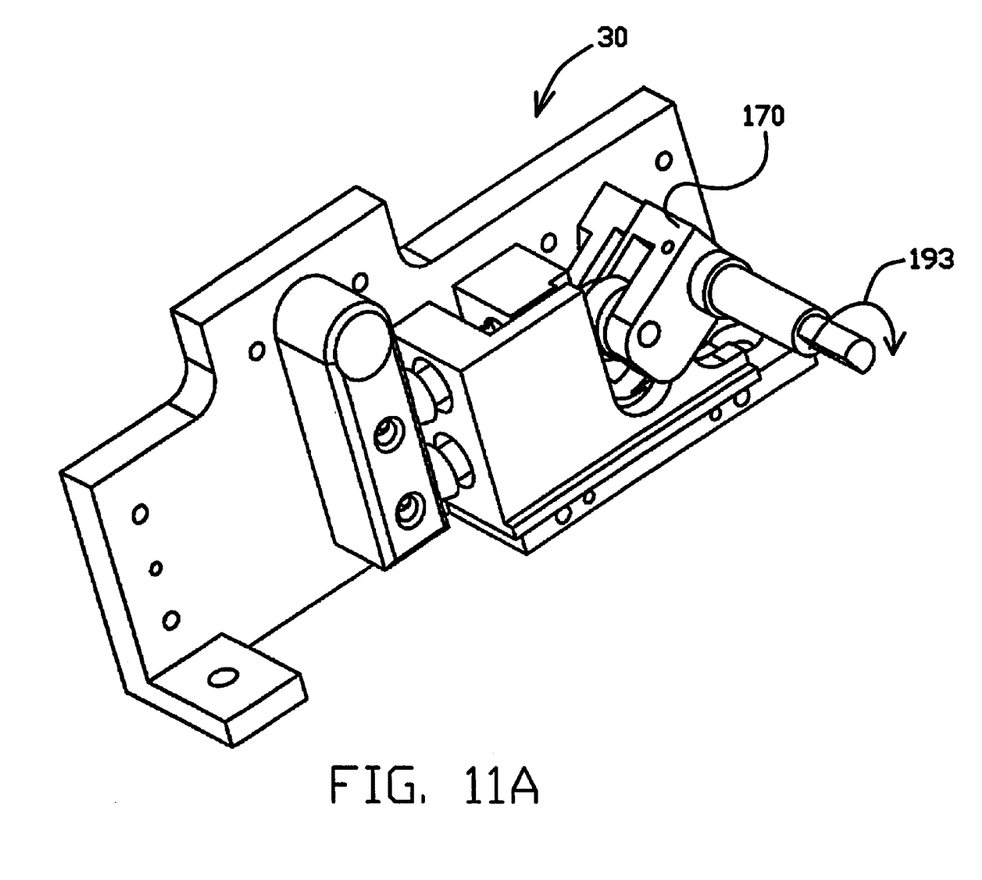
FIG. 11A is a perspective view of the optical connector latch mechanism of FIG. 9A with the bearing block advanced 60 degrees in accordance with the present invention.
Figures 11B, 11C:
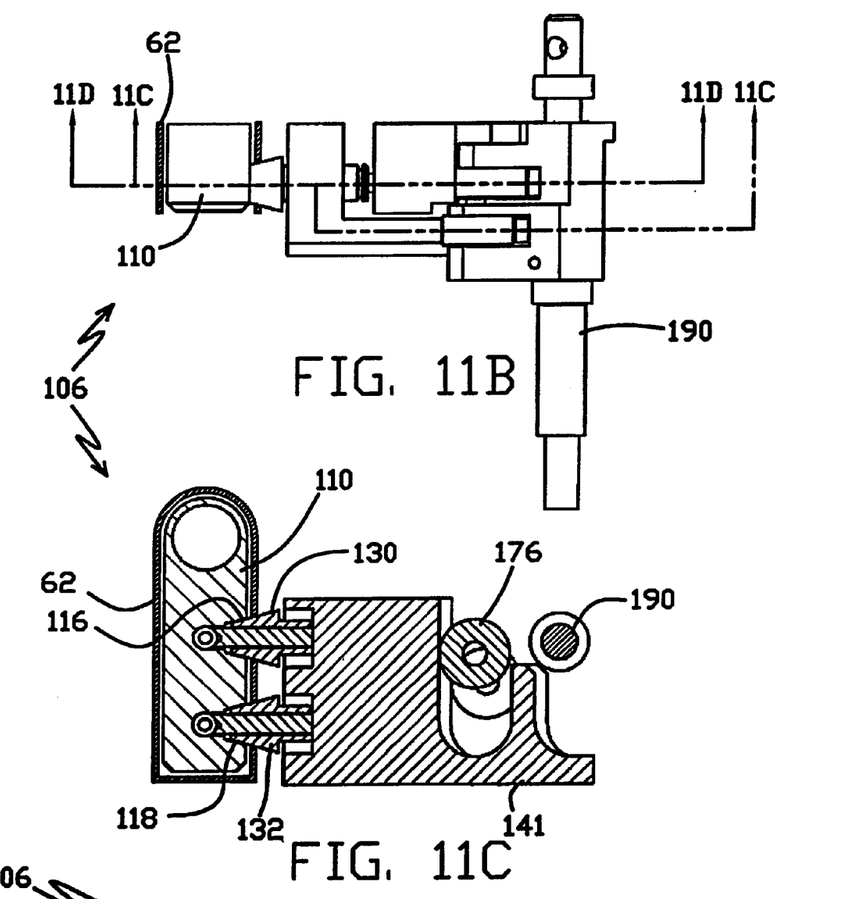
FIG. 11B is a top view of the optical connector latch mechanism of FIG. 11A.
FIG. 11C is a sectional view of FIG. 11B through the bearing block.
Figure 11D:
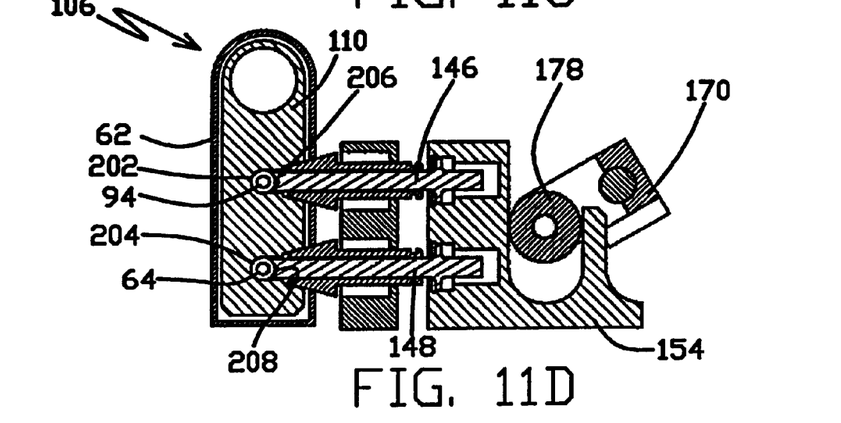
FIG. 11D is a sectional view of FIG. 11B through the ferrule block.

FIG. 11A illustrates the monitor connector 30 of the present invention with the bearing block 170 rotated approximately 60 degrees in the direction 193. FIGS. 11B–11D illustrate the optical connector latch mechanism 106 with the bearing block 170 rotated 60 degrees.

As best illustrated in FIG. 11C, the shell peg cam 176 continues to advance the shell peg block 141 towards the optics receptacle mount 110. The shell peg heads 130, 132 are now substantially fully advanced into the tapered latch holes 116, 118. In one embodiment, the shell pegs 130, 132 bottom out in the latch holes 116, 118. Simultaneously, ferrule cam 178 has advanced the ferrule block 154 towards the optics receptacle mount 110 so that the notches 206, 208 on the ferrule pins 146, 148, respectively, are fully engaged with the reference ferrule 94 and sample ferrule 64. The ends of the notches 206, 208 straddling the ferrules 94, 64 and the surfaces 202, 204 to form a three point locking system.

Figure 12A:
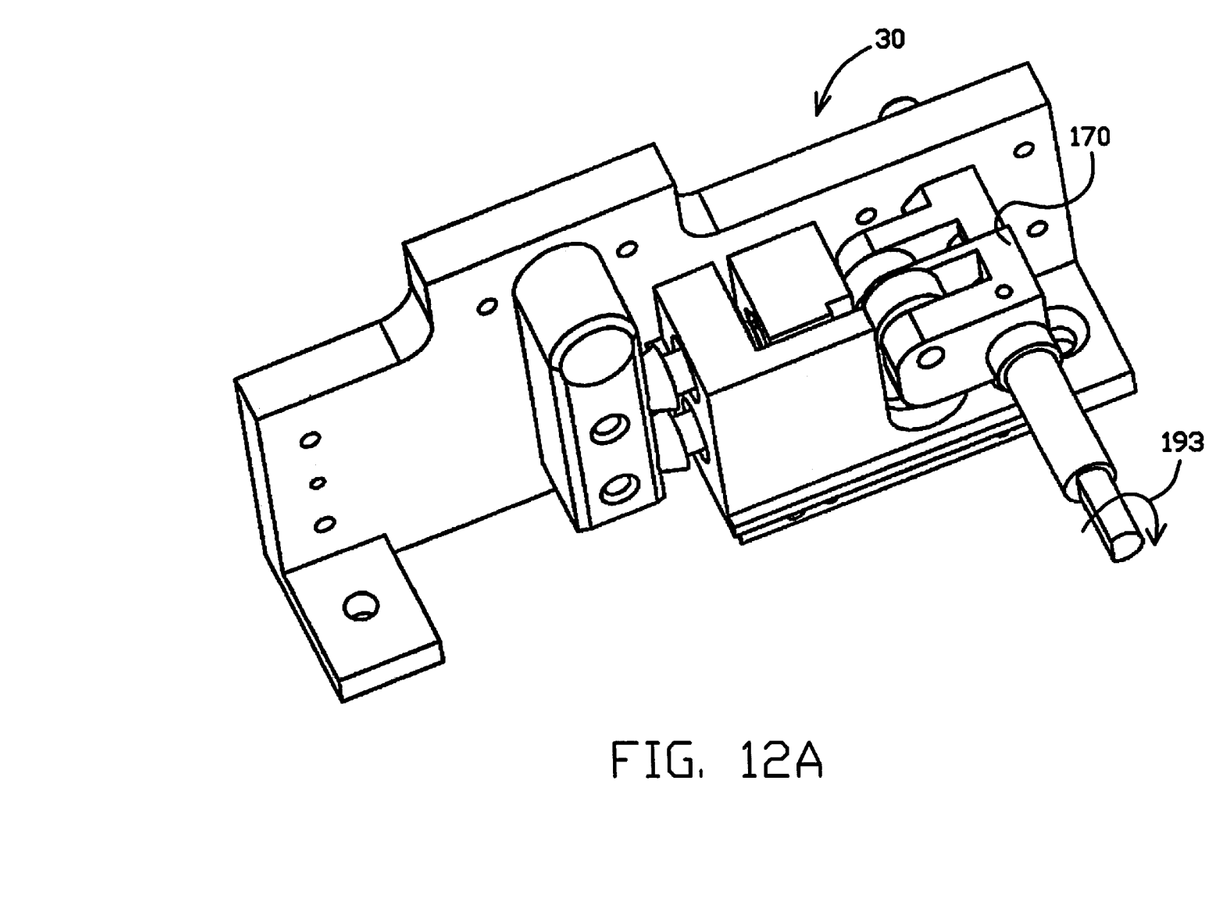
FIG. 12A is a perspective view of the optical connector latch mechanism of FIG. 9A with the bearing block advanced 90 degrees in accordance with the present invention.
Figure 12B:
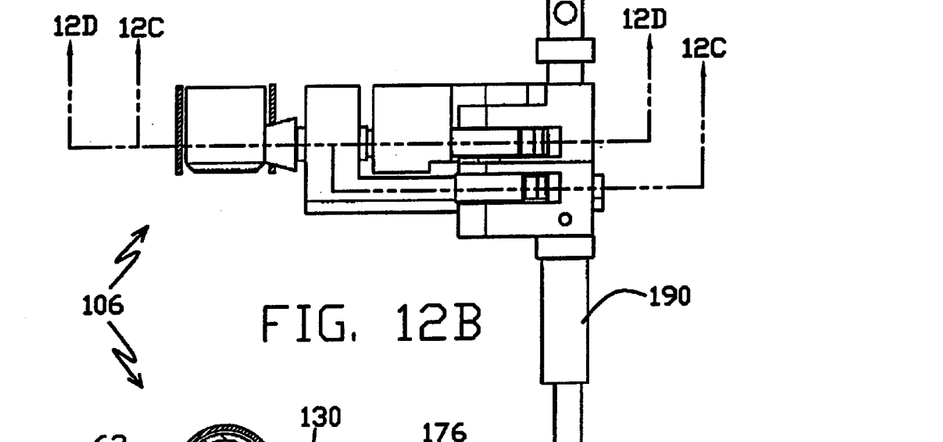
FIG. 12B is a top view of the optical connector latch mechanism of FIG. 12A.
Figure 12C:
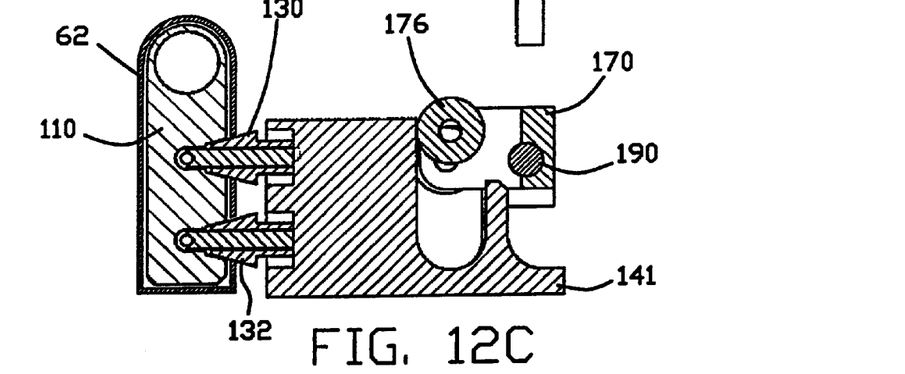
FIG. 12C is a sectional view of FIG. 12B through the bearing block.
Figure 12D:
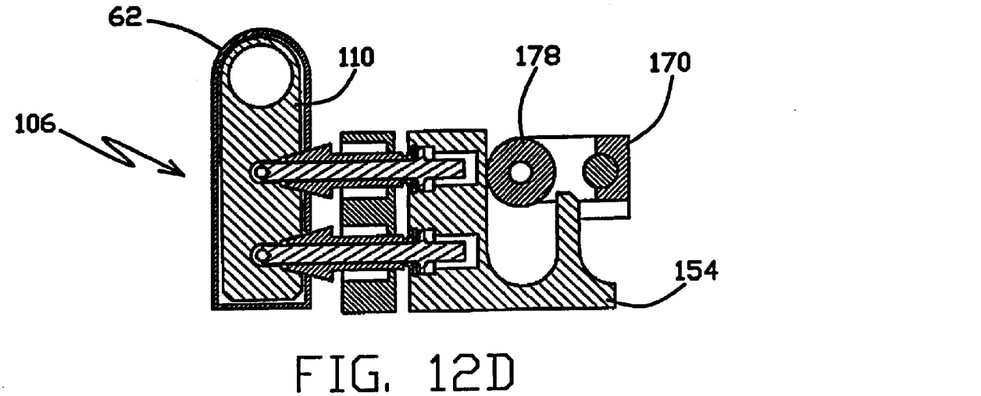
FIG. 12D is a sectional view of FIG. 12B through the ferrule block.

FIG. 12A illustrates the monitor connector 30 of the present invention with the bearing block 170 rotated approximately 90 degrees in the direction 193. FIGS. 12B–12D illustrate the optical connector latch mechanism 106 with the bearing block 170 rotated 90 degrees. In one embodiment, one of the cams 176, 178 is mounted at an angle relative to the other one, so that as the optical connector latch mechanism 106 goes through its full range of travel, it reaches a maximum displacement and then retracts slightly as the bearing block 170 reaches full travel (e.g., 90 degrees of rotation). This embodiment provides an over-center latching function that will remain locked in the latched position, regardless of forces applied to the probe connector 28. In another embodiment, both cams 176, 178 go through this over-center motion.

For example, as the bearing block 170 rotates past a certain angle (e.g., 68 degrees), shell peg block 141 reach its maximum travel, creating the maximum compression of the springs 138, 140. As the bearing block 170 continues to rotate past the certain angle (e.g., 68 degrees to 90 degrees), the shell peg block 141 will retract slightly under the force of the compressed springs 138, 140. This spring expansion provides an over-center latching mechanism. The springs 150, 152 do not extend and are compressed over the entire 90-degree rotation of the bearing block 170.

FIGS. 12A–12D illustrate the present optical connector latch 106 with the bearing block 170 rotated 90 degrees in the direction 193. The shell peg cam 176 has fully advanced the shell peg block 141 towards the optics receptacle mount 110. Similarly, the ferrule cam 178 has fully advanced the ferrule block 154 towards the optics receptacle mount 110.

The interface housing 62 can be disengaged from the monitor connector 30 by simply rotating the bearing block 170 in the direction opposite 193. The cam surfaces 176, 178 will move the shell peg block 141 and ferrule block 154 away from the optics receptacle mount 110, causing the shell pegs 130, 132 and ferrule pins 146, 148 to retract. The interface housing 62 can then be removed from the monitor connector 30.

The exact angles of handle 194 rotation and the sequence at which the mechanism events take place (e.g., when the shell pegs 130, 132 bottom out on the optics receptacle mount 110 and when the ferrule pins 146, 148 extend beyond ends of the shell pegs 130, 132) is generally not critical. All the motion happens continuously, producing the two latching functions (housing and ferrule latching).

All of the patents and patent applications disclosed herein, including those set forth in the Background of the Invention, are hereby incorporated by reference. With regard to the foregoing description, it is to be understood that changes may be made in detail, especially in matters of the construction materials employed and the shape, size and arrangement of the parts without departing from the scope of the present invention. It is intended that the specification and depicted aspects be considered exemplary only, with a true scope and spirit of the invention being indicated by the broad meaning of the following claims.

What is claimed is:

1. An optical connector latch to optically couple at least one optical fiber ferrule on an interface housing with an optics receptacle mount on an instrument, the optical connector latch comprising:
   one or more shell pegs adapted to advance the interface housing into engagement with the optics receptacle mount;
   one or more ferrule pins adapted to extend through latch holes in the interface housing and latch holes in the optics receptacle mount into engagement with the optical fiber ferrule; and
   a drive mechanism adapted to drive the one or more shell pegs and the one or more ferrule pins toward the optics receptacle mount.

2. The optical connector latch of claim 1 wherein the drive mechanism includes an operator-actuated handle.

3. The optical connector latch of claim 1 wherein the drive mechanism includes one or more cams mechanically coupled to the one or more shell pegs and the one or more ferrule pins.

4. The optical connector latch of claim 1 wherein the drive mechanism causes the one or more shell pegs to advance the interface housing into engagement with the optics receptacle mount before the one or more ferrule pins engage with the optical fiber ferrule.

5. The optical connector latch of claim 1 wherein the one or more ferrule pins extend through the one or more shell pegs.

6. The optical connector latch of claim 1 wherein the one or more shell pegs have tapered heads.

7. The optical connector latch of claim 1 wherein the interface housing has one or more holes for receiving the one or more shell pegs.

8. The optical connector latch of claim 1 wherein ends of the one or more ferrule pins comprise a shape corresponding to a shape of the optical fiber ferrule.

9. The optical connector latch of claim 1 wherein the drive mechanism includes an over-center latch.

10. The optical connector latch of claim 1 comprising shell peg springs adapted to bias the shell pegs toward the interface housing.

11. The optical connector latch of claim 1 comprising ferrule pin springs adapted to bias the one or more ferrule pins toward the optical fiber ferrule.

12. The optical connector latch of claim 1 wherein the interface housing and optics receptacle mount comprises a nested configuration when optically coupled.

13. The optical connector latch of claim 1 wherein the interface housing and optics receptacle mount comprise mating electrical connectors that electrically couple when the interface housing is advanced into engagement with the optics receptacle mount.

14. The optical connector latch of claim 1 comprising a plurality of optical fiber ferrules.

15. The optical connector latch of claim 14 comprising at least one shell peg for each optical fiber ferrule.

16. An optical connector latch comprising:
   a plurality of optical fiber ferrules on an interface housing;
   one or more shell pegs adapted to advance the interface housing into engagement with an optics receptacle mount;
   one or more ferrule pins adapted to extend through latch holes in the interface housing and latch holes in the optics receptacle mount into engagement with the optical fiber ferrule; and
   a drive mechanism adapted to drive the one or more shell pegs and the one or more ferrule pins toward the optics receptacle mount, wherein the drive mechanism causes the one or more shell pegs to advance the interface housing into engagement with the optics receptacle mount before the ferrule pins engage with the optical fiber females.

17. A method of optically coupling at least one optical fiber ferrule on an interface housing with an optics receptacle mount on an instrument, comprising the steps of:
   inserting one or more shell pegs into the interface housing and advancing the interface housing into engagement with the optics receptacle mount; and
   extending one or more ferrule pins through latch holes in the interface housing and latch holes in the optics receptacle mount into engagement with the optical fiber ferrule.

18. The method of claim 17 comprising advancing the one or more shell pegs into engagement with the optics receptacle mount before advancing the one or more ferrule pins into engagement with the optical fiber ferrule.

\* \* \* \* \*

UNITED STATES PATENT AND TRADEMARK OFFICE
CERTIFICATE OF CORRECTION

PATENT NO.     : 6,481,899 B1
DATED          : November 19, 2002
INVENTOR(S)    : Kenneth R. Quast et al.

It is certified that error appears in the above-identified patent and that said Letters Patent is hereby corrected as shown below:

Column 4,
Lines 30 and 32, delete the word "couples" and replace it with -- coupled --.

Column 10,
Line 46, delete the word "females" and replace it with -- ferrules --.

Signed and Sealed this

Fourth Day of March, 2003

JAMES E. ROGAN
*Director of the United States Patent and Trademark Office*